US011633239B2

(12) United States Patent
Ragosta et al.

(10) Patent No.: US 11,633,239 B2
(45) Date of Patent: Apr. 25, 2023

(54) LOCKING SYSTEM FOR MEDICAL DEVICE DRIVE SYSTEM

(71) Applicant: Intuitive Surgical Operations, Inc., Sunnyvale, CA (US)

(72) Inventors: Nicholas H. Ragosta, San Francisco, CA (US); Matthew A. Wixey, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 685 days.

(21) Appl. No.: 16/495,100

(22) PCT Filed: Mar. 20, 2018

(86) PCT No.: PCT/US2018/023397
§ 371 (c)(1),
(2) Date: Sep. 17, 2019

(87) PCT Pub. No.: WO2018/175467
PCT Pub. Date: Sep. 27, 2018

(65) Prior Publication Data
US 2020/0138529 A1    May 7, 2020

Related U.S. Application Data

(60) Provisional application No. 62/474,352, filed on Mar. 21, 2017.

(51) Int. Cl.
*A61B 34/30* (2016.01)
*A61B 34/35* (2016.01)
*A61B 90/00* (2016.01)
*A61B 17/00* (2006.01)

(52) U.S. Cl.
CPC .............. *A61B 34/30* (2016.02); *A61B 34/35* (2016.02); *A61B 2017/00199* (2013.01); *A61B 2017/00477* (2013.01); *A61B 2017/00973* (2013.01); *A61B 2090/035* (2016.02)

(58) Field of Classification Search
CPC ... A61B 34/30; A61B 34/35; A61B 2090/035; A61B 2017/00199; A61B 2017/00477; A61B 2017/00973
USPC ............................................................ 606/1
See application file for complete search history.

(56) References Cited

U.S. PATENT DOCUMENTS

| 8,608,045 | B2 | 12/2013 | Smith et al. |
| 9,186,142 | B2 | 11/2015 | Fanelli et al. |
| 9,439,665 | B2 | 9/2016 | Marczyk et al. |
| 9,561,045 | B2 | 2/2017 | Hinman et al. |

(Continued)

OTHER PUBLICATIONS

International Preliminary Report on Patentability for Application No. PCT/US2018/023397, dated Oct. 3, 2019, 11 pages.

(Continued)

*Primary Examiner* — Aaron F Roane
(74) *Attorney, Agent, or Firm* — Schwegman Lundberg & Woessner, P.A.

(57) ABSTRACT

A medical device drive system may include a locking structure, a locking device sized and shaped to engage with the locking structure, the locking device coupled to a drive system component, and a lifter configured to actuate the locking device into and out of engagement with the locking structure, wherein the drive system component is selectively lockable by movement of the lifter.

13 Claims, 16 Drawing Sheets

(56) References Cited

U.S. PATENT DOCUMENTS

2004/0236325 A1* 11/2004 Tetzlaff .............. A61B 18/1442
606/51
2016/0100838 A1 4/2016 Beaupré et al.

OTHER PUBLICATIONS

International Search Report and Written Opinion for Application No. PCT/US2018/023397, dated Jul. 20, 2018, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

LOCKING SYSTEM FOR MEDICAL DEVICE DRIVE SYSTEM

CLAIM OF PRIORITY

This application is a U.S. National Stage Filing under 35 U.S.C. 371 from International Application No. PCT/US2018/023397, filed on Mar. 20, 2018, and published as WO 2018/175467 A1 on Sep. 27, 2018, which claims the benefit of priority to U.S. Provisional Patent Application Ser. No. 62/474,352, filed on Mar. 21, 2017, each of which is hereby incorporated by reference herein in its entirety.

BACKGROUND

Medical device systems can include components that are driven by drive mechanisms such as electric motors. Drive components such as gears, levers, and tubes can be used to translate movement through a drive system to a medical tool. For example, surgical systems can include tools that are controlled and driven by mechanical drive systems. Surgical systems can include tools such as cutters, staplers, and cautery tools.

In some procedures, an endoscope is inserted into the patient's body to provide a view of internal organs or other features inside a patient. A procedure that involves introduction of an endoscope is called an endoscopy. A common form of endoscopy, called laparoscopy, involves insertion of an endoscope through the abdominal wall of a patient. Endoscopic and laparoscopic procedures can involve drive systems that control surgical instruments inside the patient.

SUMMARY

This document discusses, among other things a medical device drive system that includes a locking device that can be used to selectively lock an aspect of the drive system, such as a steering control.

An example medical device drive system ("Example 1") may include a locking structure, a locking device sized and shaped to engage with the locking structure, the locking device coupled to a drive system component, and a lifter configured to actuate the locking device into and out of engagement with the locking structure, wherein the drive system component is selectively lockable by movement of the lifter. The locking device may, for example, be a steering lock that locks a steering system so that an element such as an instrument may be locked in a selected configuration.

In Example 2, the medical device drive system of Example 1 may optionally be configured such that the lifter is pivotably coupled to the locking structure. In this configuration, in a first state the lifter and locking device may be pivoted toward the locking structure and the locking device is engaged with the locking structure to prevent rotational movement of the locking device relative to the locking structure, and in a second state the lifter and locking device may be pivoted away from the locking structure and the locking device is not engaged with the locking structure.

In Example 3, the medical device drive system of Examples 1 or 2 may optionally be configured such that the lifter is slidably coupled to the locking structure, wherein translating the lifter with respect to the locking structure actuates the locking device into and out of engagement with the locking structure. In an example configuration, the lifter may translate along a guide pin.

In Example 4, the medical device drive system of any one or any combination of Examples 1-3 may optionally further include a rotary input. The rotary input may include an input feature that engages a portion of the lifter to pivot or translate the lifter and actuate the locking device. In an example configuration, the input feature may include a ramp on the rotary input that engages a protrusion, lip, or pin on lifter. In another example configuration, the input feature may include a protrusion, lip, or pin on the rotary input that engages a ramp on lifter. In some examples, the medical device drive system may include one or more springs that are compressed (or extended) when the rotational input moves the lifter.

In Example 5, the medical device drive system of any one or any combination of Examples 1-4 may optionally be configured such that the rotary input is configured to couple with a computerized control system.

In Example 6, the medical device drive system of Example 5 may optionally further include comprising a control knob coupled to the lifter, wherein turning the knob moves the lifter to actuate the locking device. The control knob may optionally be coupled to the lifter with a linkage.

In Example 7, the medical device drive system of any one or any combination of Examples 1-6 may optionally further include a manual release, and the control knob may be configured to control both the locking device and the manual release.

In Example 8, the medical device drive system of any one or any combination of Examples 1-7 may optionally be configured to interface with an adaptor to operatively couple the drive system to a computerized control system.

In Example 9, the medical device drive system of Example 8 may optionally be configured such that in a first state the medical device drive system is not coupled to the adaptor and the lifter and locking device are in an unlocked position, the lifter and locking device being actuatable to a locked position, and in a second state the medical device drive system is coupled to the adaptor, the adapter is engaged with the lifter, and the lifter and locking device are in a locked position, the lifter and locking device being actuatable to an unlocked position.

In Example 10, the medical device drive system of Example 9 may optionally be configured such that the lifter is pivotably coupled to the locking structure, and in the second state the locking device is actuatable from the locked position to an unlocked position by manipulating an input that pivots the lifter.

In Example 11, the medical device drive system of any one or any combination of Examples 8-10 may optionally further include one or more springs engaged between the locking structure and the lifter, the one or more springs being compressed when the drive system is interfaced with the adaptor.

In Example 12, the medical device drive system of any one or any combination of Examples 1-11 may optionally be configured such that the locking device includes a tapered structure that includes teeth that are sized and shaped to engage with corresponding teeth on a tapered recession in the locking structure.

In Example 13, the medical device drive system of Example 12 may optionally be configured such that the teeth on the tapered structure and the corresponding teeth on the tapered recession are sized and shaped to prevent rotation of the tapered structure with respect to the tapered recession, but allow the tapered structure to both translate and pivot away from the tapered recession.

An example medical device drive system ("Example 14") may include a chassis, a locking structure coupled to the chassis, a locking device sized and shaped to engage with the locking structure, the locking device being coupled to a drive system component, a lifter coupled to the chassis, the lifter engaged with the locking device, a first input coupled to the lifter, and a second input coupled to the lifter, wherein actuation of the first input or the second input moves the lifter to engage the locking device with the locking structure and lock the drive system component.

In Example 15, the medical device drive system of Example 14 may optionally be configured such that the first input includes a manual input and the second input is configured to engage with a computerized control system.

In Example 16, the medical device drive system of Example 15, may optionally be configured to interface with an adaptor to operatively couple the drive system to a computerized control system. In an example configuration, in a first state the medical device drive system is not engaged interfaced with the adaptor and the lifter and locking device are in a neutral unlocked position and are actuatable to a locked position, and in a second state the medical device drive system is interfaced with the adaptor, the lifter and locking device are engaged with a portion of the adaptor and biased to a locked position, and in the second state the lifter and locking device are actuatable by the first input or the second input from the locked position to an unlocked position.

In Example 17, the medical device drive system of Example 16 may optionally further include one or more springs engaged with the lifter, wherein in the second state the one or more springs are compressed to accommodate movement of the lifter by the adaptor.

An Example medical device drive system ("Example 18") may include a locking structure, a locking device sized coupled to a drive system component and shaped to engage with the locking structure, and a lifter having an engagement end coupled to the locking device, the lifter being movable relative to the locking structure. The system may be configured such that in a first state the engagement end of the lifter is biased toward the locking structure and the locking device is engaged with the locking structure such that the drive system component is not drivable, and in a second state the engagement end of the lifter is biased away from the locking structure and the locking device is disengaged from the locking structure such that the drive system component is drivable.

In Example 19, the medical device drive system of Example 18 may optionally be configured such that the lifter is pivotable with respect to the locking structure to move the lifter and locking device between the first state and the second state.

In Example 20, the medical device drive system of Example 19 may optionally be configured such that the drive system component includes a steering control, the steering control being lockable by the locking device. The medical device drive system may further include a manual release input, the manual release input being coupled to the lifter, wherein actuating the manual release locks the steering control.

An example (e.g., "Example 21") of subject matter (e.g., a system or apparatus) may optionally combine any portion or combination of any portion of any one or more of Examples 1-20 to include "means for" performing any portion of any one or more of the functions or methods of Examples 1-20, or a "machine-readable medium" (e.g., massed, non-transitory, etc.) including instructions that, when performed by a machine, cause the machine to perform any portion of any one or more of the functions or methods of Examples 1-20.

Each of these non-limiting examples can stand on its own, or can be combined in various permutations or combinations with one or more of the other examples. This Summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Medical device drive systems can be used to control an instrument that is coupled to a drive system with a shaft. A teleoperated surgical system, for example, can employ a medical device drive system to control a surgical instrument that can be inserted into a patient to perform a surgical procedure.

Manipulation of a surgical instrument during a teleoperated surgical procedure can be difficult, due to factors such as space constraints, the size of components, the need for precision and accuracy during surgery, and the presence of multiple tools in the body.

The present inventors have recognized, among other things, that a locking device can be constructed from a locking device (such as a steering lock) that can be actuated by a lifter, which in turn can be actuated by a manual input, a rotary input, or both, and controls optionally integrated with telerobotic control system, release mechanisms, or both. Springs can optionally be configured to bias the lifter toward a locked or unlocked position.

The locking device can engage another component, such as a mounting plate, which can include one more features that engage features on the locking to prevent the locking device from turning, for example. In various configurations, the lifter can translate or pivot to move the steering lock. The lifter can be actuated by an input mechanism, such as a manual switch, a rotary input, or a linkage, that can pivot or translate the lifter. In various configurations, the lifter can be biased toward a locked position, or an unlocked position. In some examples, the lifter can be actuated by installing a locking plate onto an interface with a control system, and the lifter can be actuated by an robot-assisted control, manual control, or both. In some examples, a single lifter can engage two locking devices to simultaneously lock two inputs. In some examples, the locking device can include an angled or tapered feature such as a cone that can releasably engage with matching features on a mounting plate to prevent rotation, but permit disengagement by translating or pivoting the locking device away from the matching features on the mounting plate.

Figure 1A:
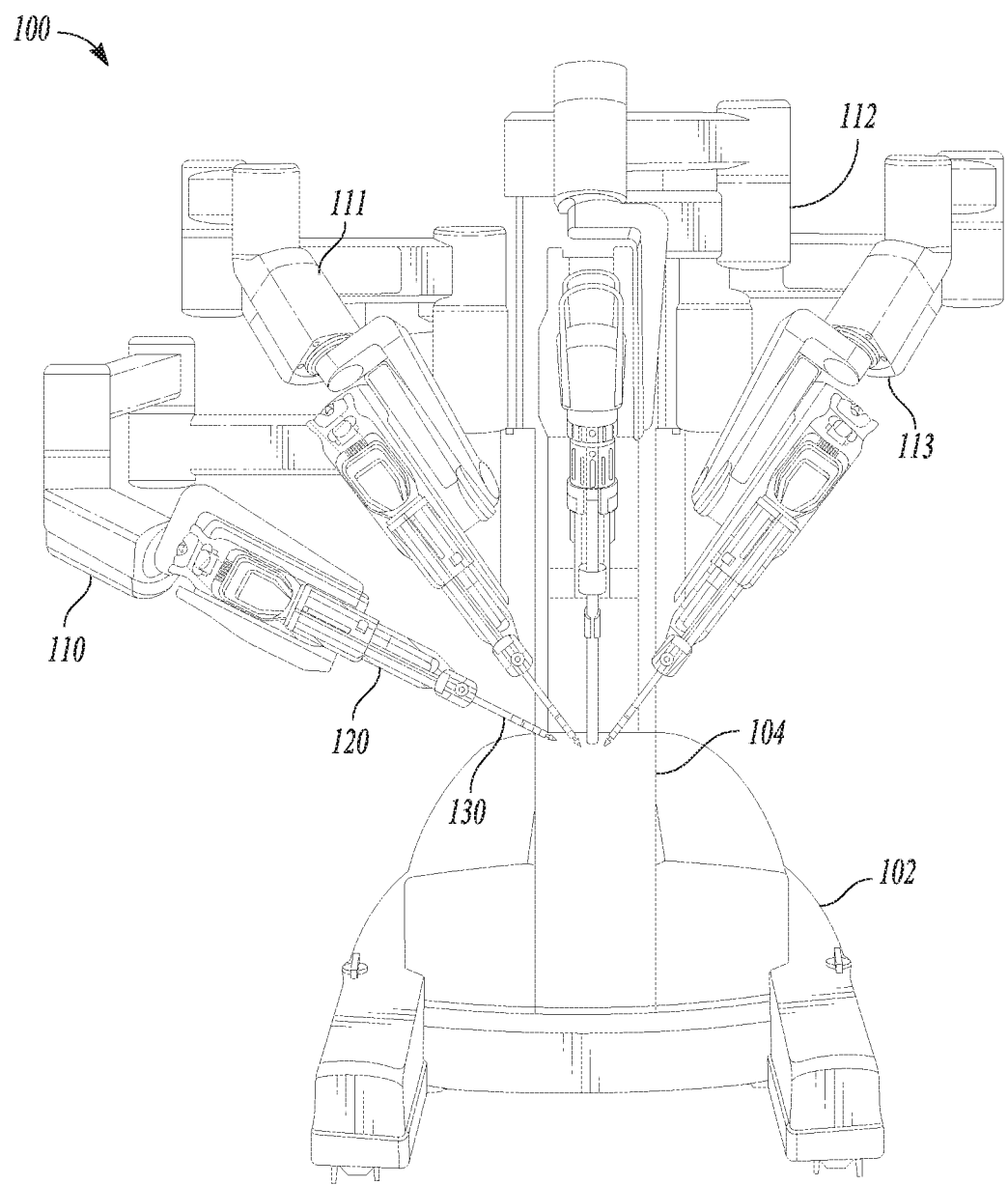
FIG. 1A is an illustration of an example instrument system for use in robot-assisted minimally invasive surgery.
Figure 1B:
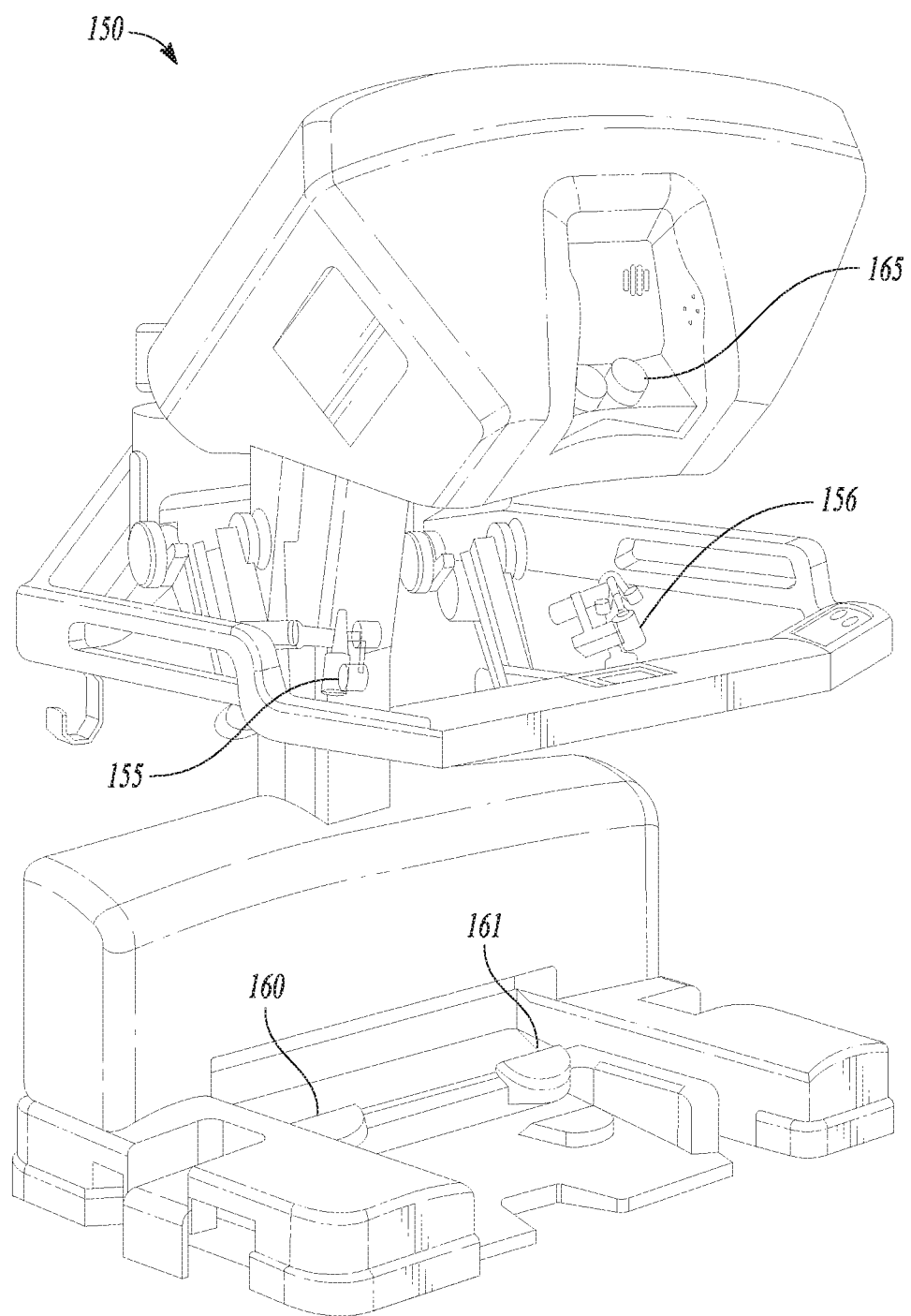
FIG. 1B is an illustration of an example physician console for use in robot-assisted minimally invasive surgery.
Figure 1C:
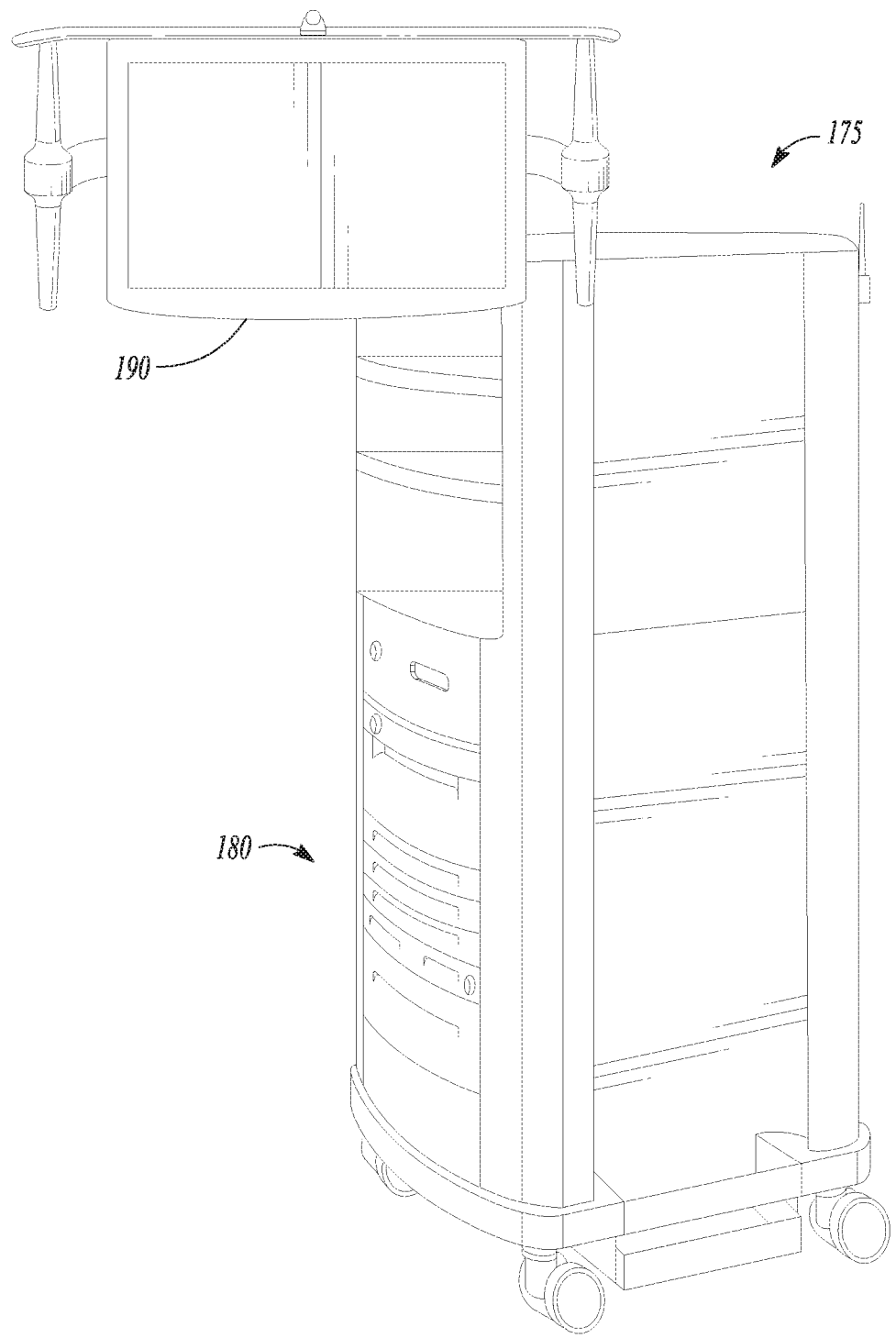
FIG. 1C is an illustration of an example control cart for use in robot-assisted minimally invasive surgery.

FIGS. 1A, 1B, and 1C illustrate an example robot-assisted minimally invasive surgical system. FIG. 1A shows an instrument system 100 (sometimes known as a "patient side cart") that can be situated near a patient operating table (not shown). FIG. 1B shows a surgeon console 150 that can include controls and a viewing system. FIG. 1C shows a control cart 175 that can include, for example, processing equipment and communication equipment.

Referring again to FIG. 1A, the system 100 can include a base 102, a support tower 104, and one or more manipulator arms 110, 111, 112, 113, which can be mounted on the support tower. Alternatively, the manipulator arms 110, 111, 112, 113 can be connected to a main boom (not shown), which can be movable. An instrument 130 can be mounted to an instrument mount 120 on one of the manipulator arms. A cannula (not shown in FIG. 1A) can be mounted to a cannula mount. An instrument 130 can be inserted through a cannula seal in the cannula, and into the patient (not shown) for use in a surgical or other medical procedure. Through movement of the manipulator arms, the orientation of the instrument can be controlled in multiple dimensions, e.g. lateral, horizontal, vertical, angular movements in one, two, or three planes.

FIG. 1B shows an example physician console 150. The physician console can include hand control 155, 156 and pedal controls 160, 161. The hand controls 155, 156, and pedal controls 160, 161 can be used to control equipment at the patient side cart. For example, portions of a distal end of an instrument can be manipulated using instrument controls. The controls can include haptic feedback features so that a physician can interpret physical information, such as resistance or vibration, through the controls. The physician console 150 can also include a viewing system 165 that can display video or other images of a surgical site.

FIG. 1C shows an example control cart 175. The control cart can include processing equipment 180 for processing controls, facilitating communication between the physician console and the patient side cart, or a remote site. The control cart 175 can also include a display 190, which can show images that the physician is seeing on the physician console, a video feed from a camera in the patient, or other information. In an example configuration, signals input at a surgeon console 150 can be transmitted to the equipment 180 on the control cart, which can interpret the inputs and generate commands that are transmitted to the patient side cart 100 to cause manipulation of an instrument 130 or portions of a manipulator arm 110. The equipment 180 is shown on a cart for exemplary purposes, but could also be arranged in various configurations, e.g., it could be integrated as part of the physician console, the patient side cart, or both, or divided between the physician console and patient side cart. The equipment can also be provided as software, hardware, or both, on an installed or remote system.

Figure 1D:
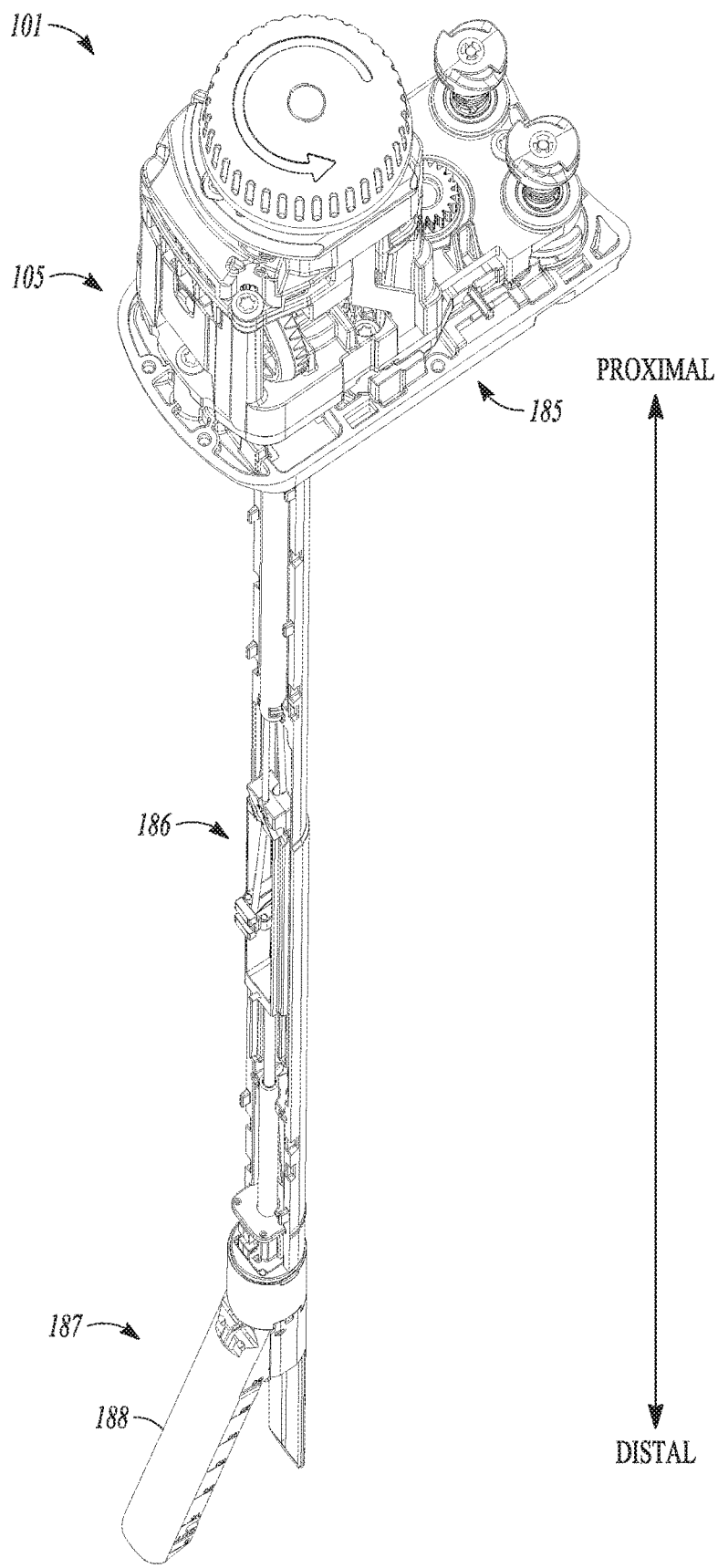
FIG. 1D is a perspective view of an example medical device drive system connected to an example medical tool.

FIG. 1D shows an example medical device system 101 that can be mounted on and used with the instrument system 100 shown in FIG. 1A. The medical device system 101 can include a proximal portion 105 including an interface 185 that can couple to a computerized control system such as the system illustrated in FIGS. 1A, 1B, and 1C, a middle portion 186 that can include drive components such as a drive member (not shown in FIG. 1D), and a distal portion 187 that can include an surgical tool 188. The surgical tool 188 can, for example, be any of a variety of surgical tools, such as a cutter, grasper, a cautery tool, a camera, a light, or a surgical stapler. The surgical tool 188 can be the instrument 130 shown in FIG. 1A. For the purpose of this document, the terms "tool" and "instrument" are interchangeable.

Figure 2:
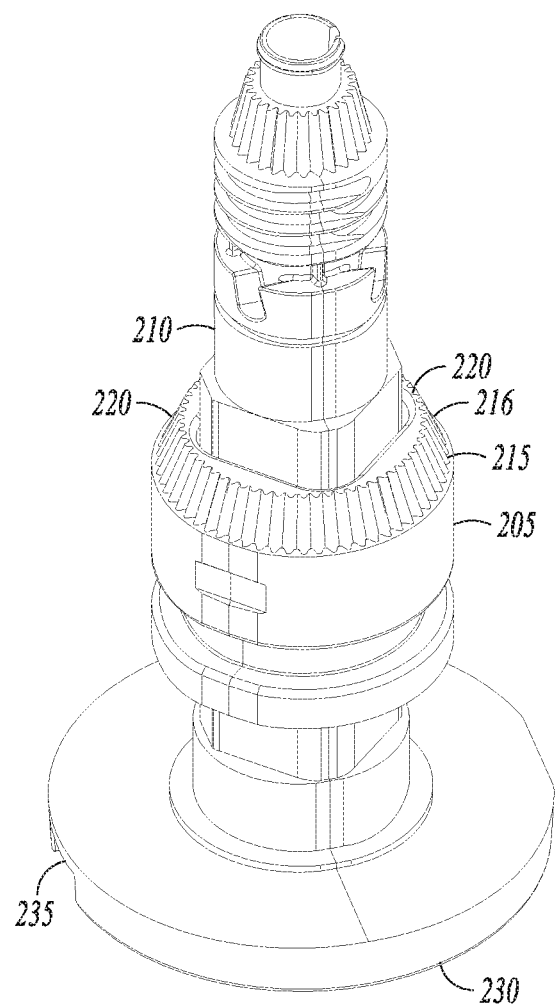
FIG. 2 is a perspective view of a locking device for use with a medical device drive system.

FIG. 2 is a perspective view of a locking device 200 for use with a medical device drive system. The locking device may include a body 205 that is coupled to a shaft component 210 of a medical device drive system. The shaft component 210 may, for example, be a portion of a steering control system, and the various locking systems described herein may lock the steering system to prevent steering movement of a surgical instrument or other steerable component.

The locking device 200 may include a locking feature 215 that is sized and shaped to engage with a corresponding locking structure 305 (shown in FIG. 3) on another part, such as a structural component. In an example configuration, the body 205 may extend around the shaft component 210, and the locking feature may include a plurality of locking structures 216 at locations distributed around the shaft component to enable the locking feature 215 to engaged the locking structure 305 in a variety of rotational positions. In an example, the locking feature 215 can include a plurality of teeth 220 that are sized and shaped to engage teeth 320 on the locking structure 305. The locking feature 215 may be formed in a tapered portion 220 of the locking device 205 to facilitate movement of the locking feature into and out of engagement with the locking structure 305. The tapered portion 220 may, for example, be a frustum. The tapered portion may alternatively be rounded, e.g. convex or concave. The shaft 210 may couple to a bottom portion 230 that may include an interface 235 to couple the shaft to a computerized control system, such as a telerobotic surgical system. The locking device may also include an engagement feature 225 such as a groove that is sized and shaped to engage with a lifter 405 (shown in FIGS. 4 and 5.)

Figure 3:
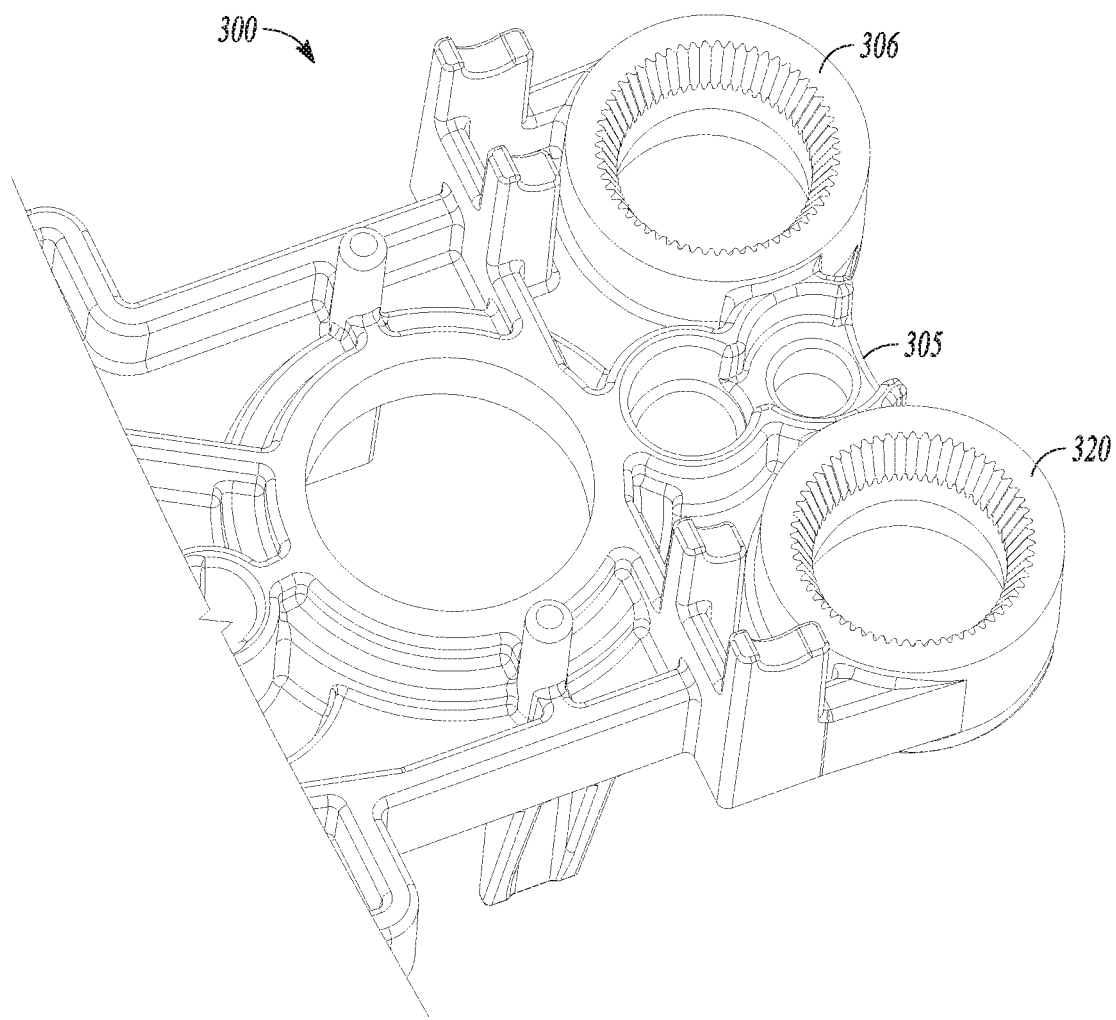
FIG. 3 is a perspective view of a bottom side of a mounting plate that is configured to interface with the locking device shown in FIG. 2.

FIG. 3 is a perspective view of a bottom side of a component 300 that is configured to interface with the locking device 200 shown in FIG. 2. The component can, for example, be a mounting plate or chassis onto which other components may be mounted. The component 300 can include a locking structure 305 that is sized and shaped to engage with the locking device 205 shown in FIG. 2. In an example where the locking device 205 includes a plurality of teeth 220, the locking structure 305 can include a plurality of matching teeth 320 that are sized and shaped to engage with teeth 220 on the locking device 205 to enable locking engagement at various rotational positions. The circumferential arrangement of teeth 220, 320 may allow the locking structure locking device 205 to engage with the locking structure 305 at any rotational position with minimal rotation necessary to align teeth 220 with teeth 320 on the locking structure. The locking structure 305 may, for example, be recessed, and may be sized and shaped receive the locking device 205 into the recession. In another configuration (not shown), the locking structure may protrude from the component 300 and extend into a recession in the locking device 205 (i.e., the structure of the components can be reversed). The component 300 may optionally include a second locking structure 306 that is sized, shaped, and positioned to engage with a second locking structure (shown in FIG. 9C).

Figure 4:
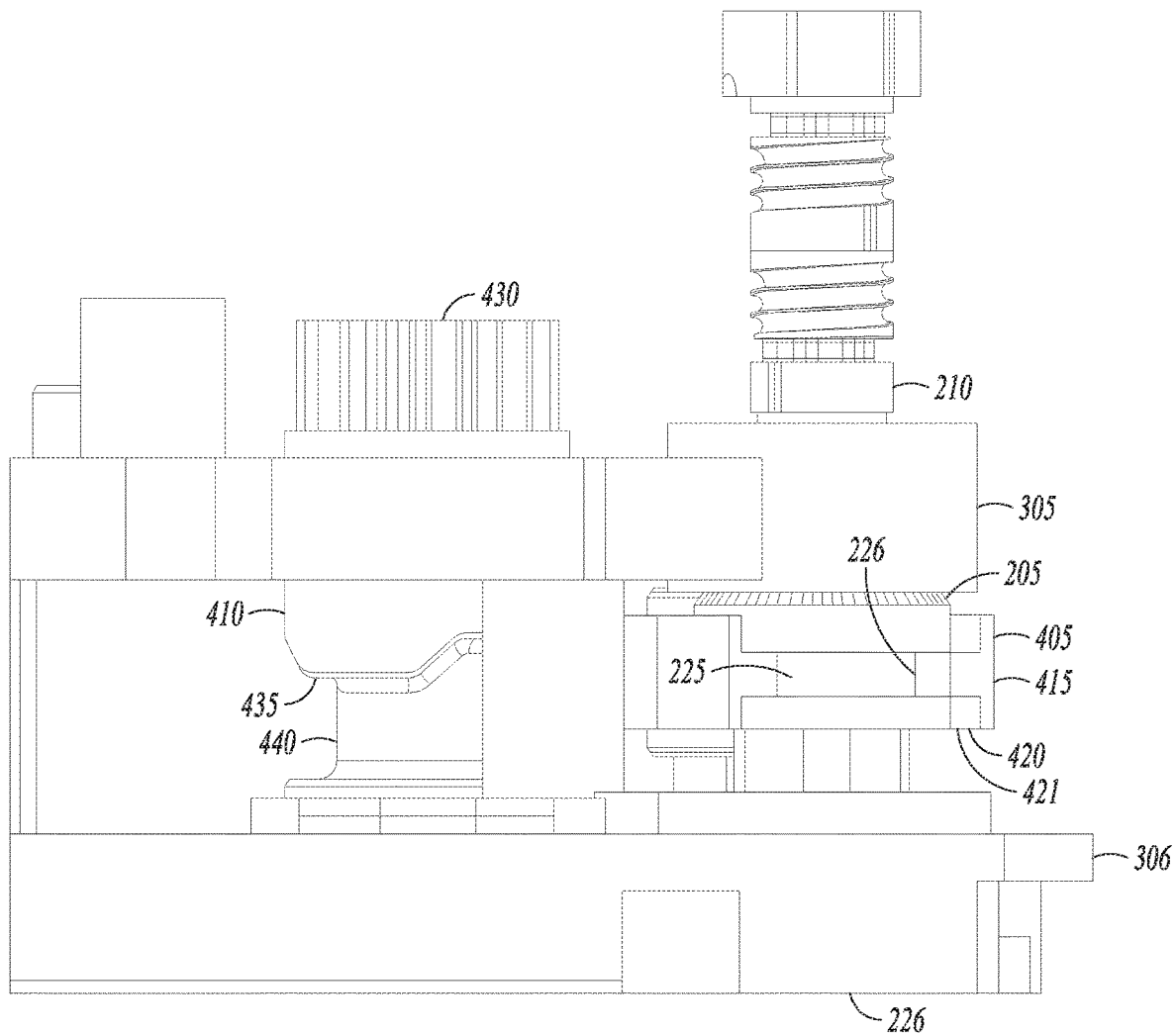
FIG. 4 is a side view of a locking device assembled with a mounting plate, lifter, and tensioning input.
Figure 5:
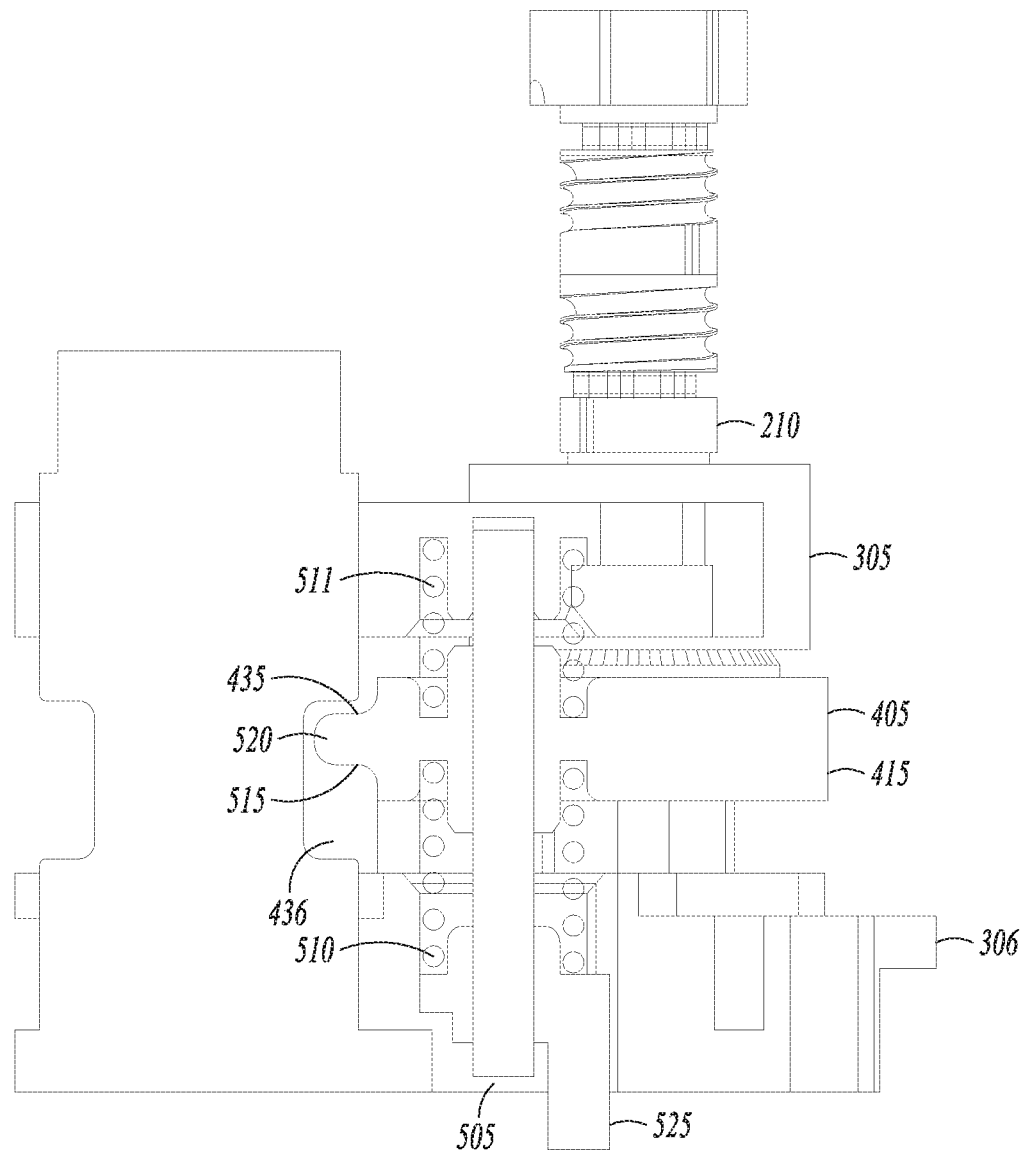
FIG. 5 is a cross-sectional view of an example configuration that includes a lifter assembled with a locking device, tensioning input, mounting plates, guide pin, and springs.

FIG. 4 is a right-side view of a locking system 400 in which the locking device 205 is assembled with a mounting plate locking structure 305, lower chassis 306, a lifter 405, and input 410. FIG. 5 is a front cross-sectional side view of an example configuration that includes the lifter 405 assembled with the locking device 205, the input 410, mounting plate locking structure 305, a guide pin 505, and a first spring 510, and a second spring 511. The lifter 405 may slide up and down on the guide pin 505. In a first state, the lifter 405 is in an up position, and the locking device 205 is engaged with the locking structure 305 to lock the shaft 210. In a second state, the lifter is in a down position, and the locking device is disengaged from the locking structure 305, allowing the shaft to rotate.

FIG. 4 is rotated counter-clockwise on a vertical access relative to the side view of FIG. 5 to show the first (right) end 415 of the lifter 405 engaged with the locking device 205. The lifter 405 can include an engagement feature 420 (e.g. a protrusion such as a lip) that is sized and shaped to engage with the engagement feature 225 (e.g., groove) on the locking device 405. While the system is illustrated with groove 226 on the locking device 205 and a lip 421 extending around an inner surface of the lifter 405, other configurations are possible. For example, in an alternate configuration (not shown), one or more protruding lips or other on the locking device may extend into one or more recessions (such as grooves) on the lifter 405.

In various configurations, the locking system 400 may be configured so that the lifter 405 and locking device 205 are in a neutral locked (i.e. up) position, or are in a neutral unlocked (i.e. down) position. A switch 525 may be configured to displace the lifter 405 and locking device 205 upward. The switch 525 may be actuated, for example, by a manual switch input, or by a feature (e.g., latch) on an adaptor that couples the locking system 400 to a computer control system (e.g., telerobotic-assisted control system). The lifter may also be actuated by an input 410, which may be manually driven, or driven using a computer-controlled system that drives a gear 430 that may be coupled to the input 410. In some example, the switch 525 and input 410 may be configured to cooperate, e.g. the locking system 400 may be configured to be in an unlocked neutral state, the switch 525 may bias the system 400 into a locked state, and the input 410 may, when the switch 525 is activated, selectively bias the system from the locked state to the unlocked state.

As shown in FIG. 5, the input 410 and lifter 405 may be sized and shaped so that rotation of the input 410 moves a second end 515 of the lifter. For example, the lifter 405 may include a feature 520 such as a protrusion that engages a feature 435 such as a lip on the input 410. As the input 410 is rotated counter-clockwise (as viewed from above), the protrusion encounters a ramp 440 on the lip 435 that pushes the protrusion 520 down and disengages the locking device 205 from the locking structure 305.

In an example configuration, when the switch 525 is not engaged, and the lifter is in a down position so that the locking device 205 is not engaged with the locking structure, a lower lip 436 on the input can engage the protrusion 520 and impart an upward force on the protrusion 520 and lifter 405 to press the locking device 205 into engagement with the locking structure. In this example, the input 410 can thus serve to selectively unlock the system 400 when the switch is engaged, and can selectively lock the system 400 when the switch is not engaged.

In an example configuration where the springs 510, 511 are configured to bias the lifter 405 upward on the guide pin 505 to a locked state, turning the input 410 clockwise allows the lip 520 to move up the ramp 440 in response to net spring forces acting on the lifter 405, which allows the lifter 405 to be displaced upward (proximally) and pushes the locking device 205 into engagement with the locking structure 305. Other configurations are possible. For example, in an alternate configuration, the springs 510, 511 may be configured to bias the lifter downward to an unlocked state, and the may ramp be configured to bias the lifter 405 upward to engage the locking device 205 with the locking structure 305. The location and spring constants of the springs 510, 511 may be selected to provide a neutral position for the lever that is in the locked state, or the unlocked state.

In an example configuration, the first spring 510 may have a spring constant that is higher than the second spring 511. When the switch 525 is actuated, the switch imposes a force on the first spring 510, which conveys the force to the lifter 405 and the second spring 511. Because the second spring 511 has a spring constant that is lower than the first spring 510, the second spring 511 compresses more than the first spring 510, and the lifter moves upward toward the second spring. As previously described, the input 410 may be configured to press the lifter 405 downward to disengage the locking device 205 from the locking structure 305.

The lifter 405 and other components can be configured to have different neutral states when the system is coupled to a computerized control system ("on-system") or not coupled to a computerized control system ("off-system"). In an example arrangement, the lifter 405 and other components of the locking system 400 can be arranged to be unlocked in a neutral state off system (with the lifter translatable to a locked condition), but biased to a locked condition in a neutral state when on-system (e.g. when coupled to an adaptor that connects to the computerized control system pushes the lifter upward) and pivotable on-system to an unlocked condition, for example by actuation of the input 410 to push the lifter 405 down away from the locking structure. For example, when the locking system 400 is unlocked in a neutral state, the input 410 can be configured to overcome the force of spring 511, and optionally also forces from spring 510, to bias the lifter 405 upward to engage the locking device 205 with the locking structure 305. When the locking system is locked in a neutral state (e.g. on-system), the input 410 can selectively press the lifter 405 downward to disengage the locking device 205 from the locking structure 305.

Figure 6:
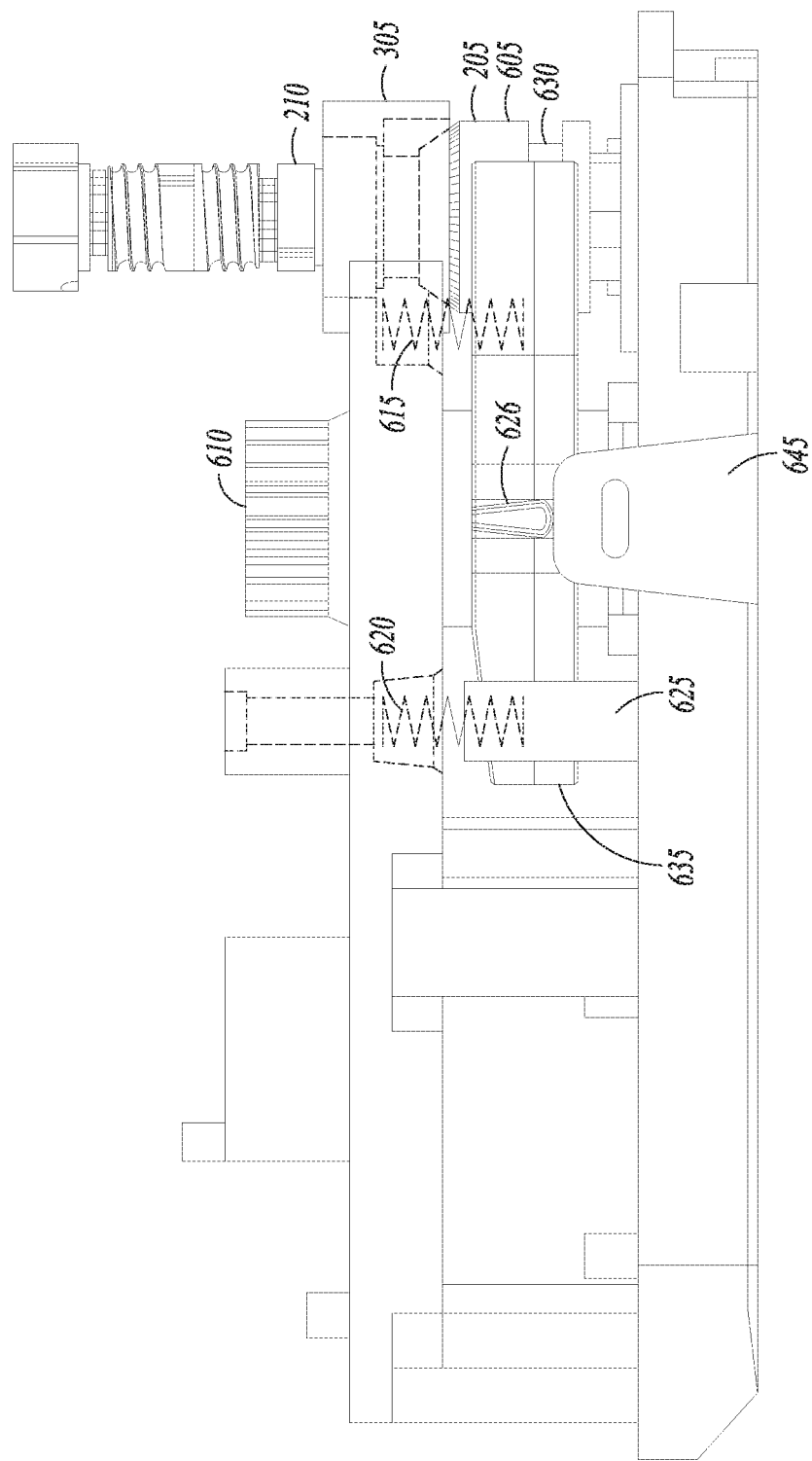
FIG. 6 is a side view of an example configuration that includes a pivoting lifter and springs.

FIG. 6 is a side view of an example locking system 600 that includes a pivoting lifter 605 having a first end 630 engaged with locking device 205. The locking device 205 is shown in an upward, locked position, with the locking device 205 engaged with the locking structure 305 to prevent rotation of the locking device 205 and shaft 210. The lifter 605 can be pivoted downward. As the first end 630 of the pivoting lifter 605 moves downward, the locking device 205 moves out of engagement with the locking structure 305, which allows the locking device 205 and shaft 210 to rotate.

Various lifter mounting arrangements are possible, including pivoting arrangements, and arrangements where the lifter 605 both translates and pivots. In some examples, the lifter 605 can pivot on springs 615, 620. The lifter 605 can optionally pivot on a fulcrum, which can, for example be a portion of the lifter that engages the adapter 645. In some examples, the lifter can optionally be coupled to a pin or shaft that is coupled to one or both of the mounting plates 305, 306, for example at element 625 or near the center of the lever 626. In some examples, as shown in FIG. 9C, a pin 940 can be coupled to the lifter 605 and positioned in a slot 950 that allows the lifter and pin to pivot around the pin and slide in the slot 950.

In the configuration illustrated in FIG. 6, the lifter 605 may be coupled to two springs 615, 620. In an example, the first spring 615 requires less force to compress or extend than is required by the second spring 620, i.e. the first spring 615 has a lower spring constant than the second spring 620.) When an upward force is imposed on the lifter 605 between the first spring 615 and the second spring 620, the first spring 615 compresses and the first end 630 of the lifter 605 pivots upward to engage the locking device 205 with the locking structure 305.

In an example configuration, the lifter 605 may be moved upward by a push member 645, which may for example be a portion of a manual switch, or a latch on an adaptor that is configured to couple the locking system 600 to a computerized control system (e.g. telerobotically-assisted surgical system). In some examples, the push member 645 biases the lifter 605 upward, compressing the first spring 615 a first distance and compressing the second spring a second distance that is less than the first distance, with the net effect that the first end 630 is moved toward the locking structure 305 to engage the locking device 205 with the locking structure.

Figure 7:
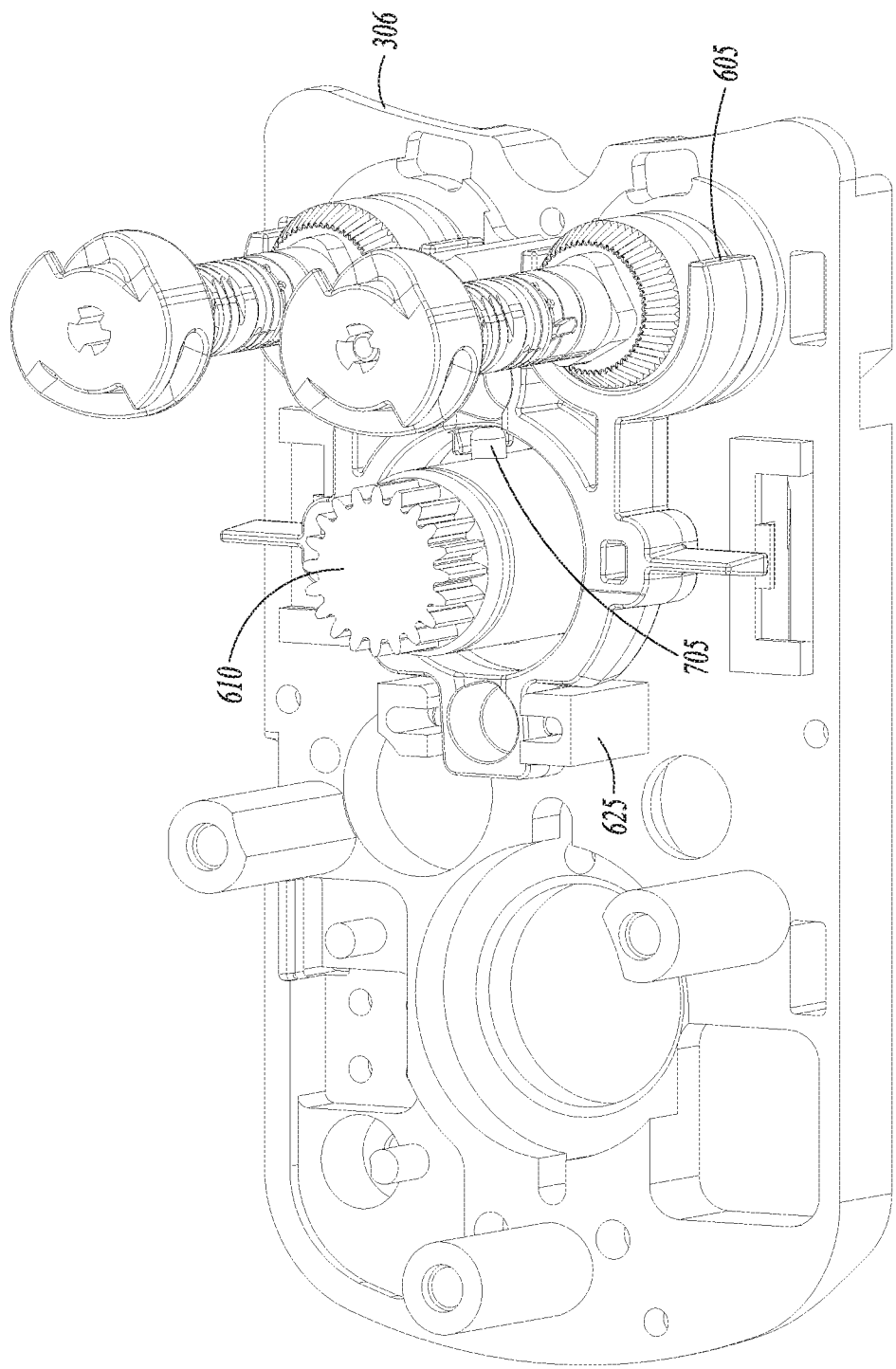
FIG. 7 is a perspective view of a tensioning input that has an engagement feature that engages a lifter.

The lifter 605 may also be pivoted by an input 610, which may for example be a rotary input that can be actuated by a computerized control system, or manually, or both. An engagement feature such as a protrusion, recession, or lip on the input 610 may engaged a corresponding engagement feature on the lifter 605 when the input is actuated (e.g., rotated). For example, a protrusion on the input 610 (as illustrated in FIG. 7) may interact with a ramped lip on the lifter 605 to bias the lifter down when the input is rotated in a first direction and allow the lifter to move up (e.g., as driven by a spring force) when the input is rotated in a second direction. In an example, from a locked position imposed by the push member 645, the lifter 605 may be pivoted downward to move the first end 630 of the lifter 605 away from the locking structure 305 to release the system lock.

The lifter 605 and other components can be configured to have different neutral states when the system is coupled to a computerized control system ("on-system") or not coupled to a computerized control system ("off-system"). In an example arrangement, the lifter 605 and other components of the locking system 600 can be arranged to be unlocked in a neutral state off system (with the lifter pivotable to a locked condition), but biased to a locked condition in a neutral state when on-system (e.g. when coupled to an adaptor that connects to the computerized control system) and pivotable on-system to an unlocked condition, for example by actuation of the input 610. For example, when the locking system 600 is unlocked in a neutral state, the input 610 can be configured to overcome the force of spring 615, and optionally also forces from spring 620, to bias the pivoting lifter 605 upward to engage the locking device 205 with the locking structure 305. When the locking system is locked in a neutral state (e.g. on-system), the input 610 can selectively press the lifter 605 downward to disengage the locking device 205 from the locking structure 305.

FIG. 7 is a top perspective view of the configuration shown in FIG. 6. The input 610 can have an engagement feature 705 that can engage the lifter 605. The engagement feature 705 can, for example, be a pin or other protrusion that engaged a feature such as a ramp on the lifter. In an example configuration, as the input is rotated, the engagement feature 705 may push the lifter 605 upward (overcoming force from spring 615) to press the locking device 205 into engagement with the locking structure 305. In another example configuration, rotation of the input 610 may move the engagement feature 705 to allow the spring 615 to push the lifter 605 upward (e.g. the engagement feature may slide up a ramp on the locking device 205), and when the input is rotated back in an opposite direction, the engagement feature may push the lifter downward and move the locking device 205 out of engagement with the locking structure. The input 610 may be driven via gear 705, may be manually driven (e.g. by turning a knob, not shown), or both.

Figure 8A:
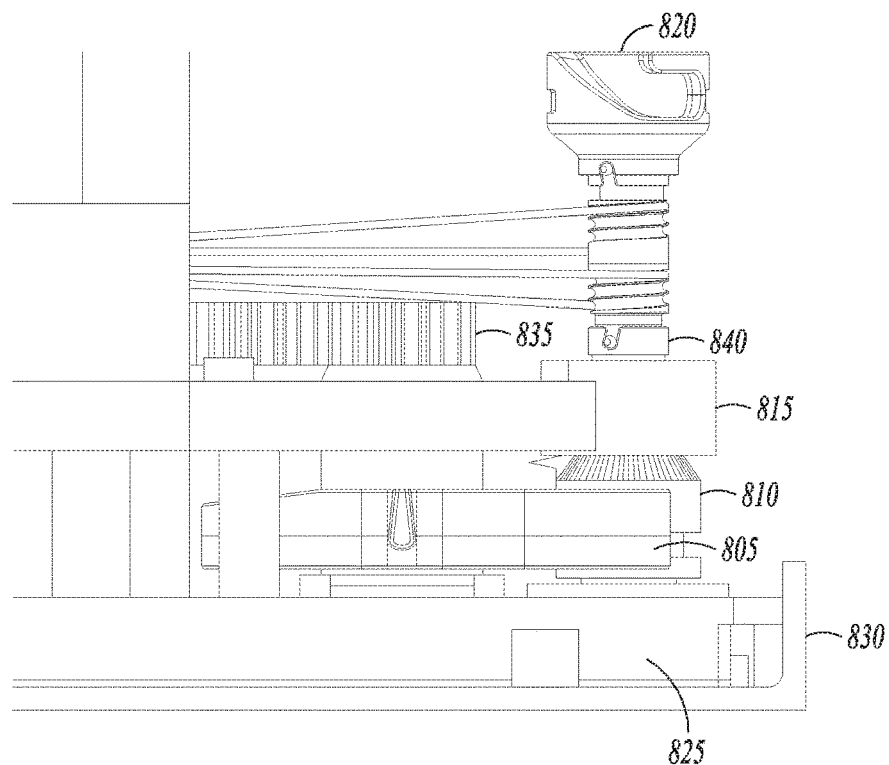
FIG. 8A is a side view of a lifter and locking device.
Figure 8B:
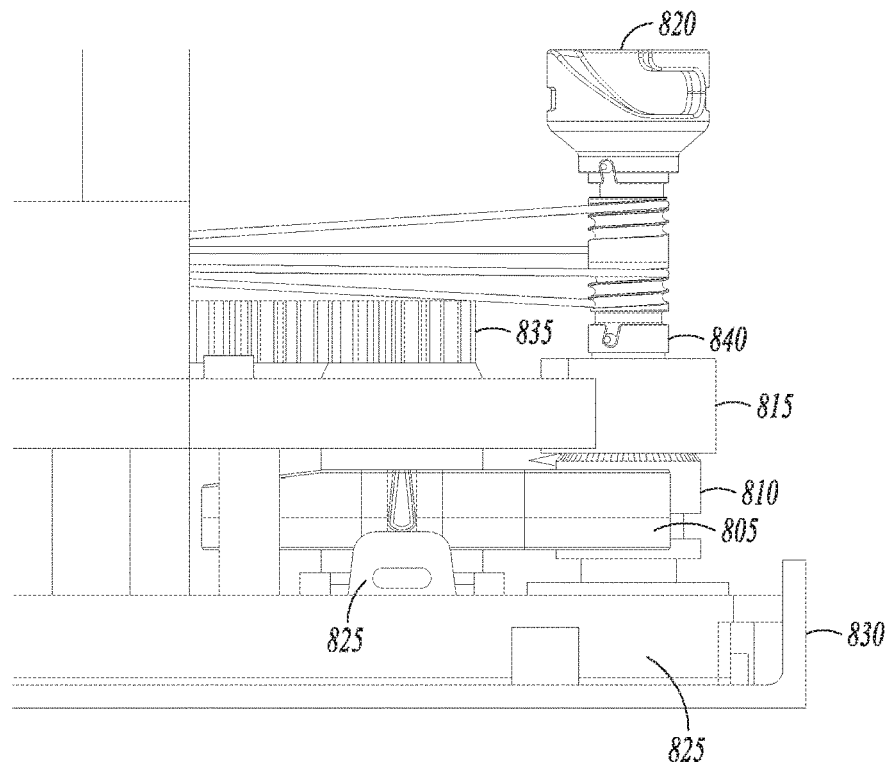
FIG. 8B is a side view of a lifter and a locking device with the lifter biased up to lift the locking device into engagement with a mounting plate.
Figure 8C:
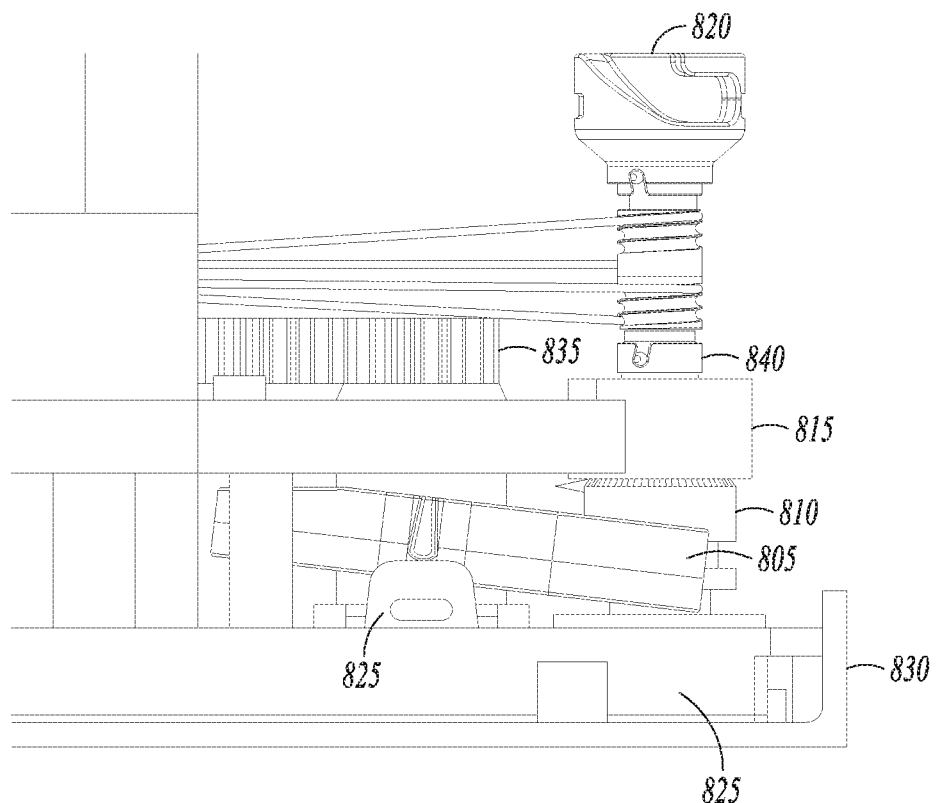
FIG. 8C is a side view of a lifter and a locking device with an input actuated to pivot the lifter down to disengage the locking device from the mounting plate.

FIG. 8A, FIG. 8B, and FIG. 8C are side views of a locking system that includes a lifter 805 and locking device 810 configured to couple with locking structure 815. The locking system 800 can be configured, for example, in the same manner as locking system 600. In FIG. 8A, the lifter 805 is in a down position, and the locking device 810 is not engaged with the locking structure 815. In FIG. 8B, the lifter 805 is moved upward by a latch 825 on an adaptor 830 (shown in 8C), and the locking device 810 is engaged with locking structure 815 to prevent the rotation of shaft 840 on steering control 820. In FIG. 8C, the input 835 has been actuated to pivot the lifter 805 downward to disengage the locking device 810 from the locking structure 815.

Figure 9A:
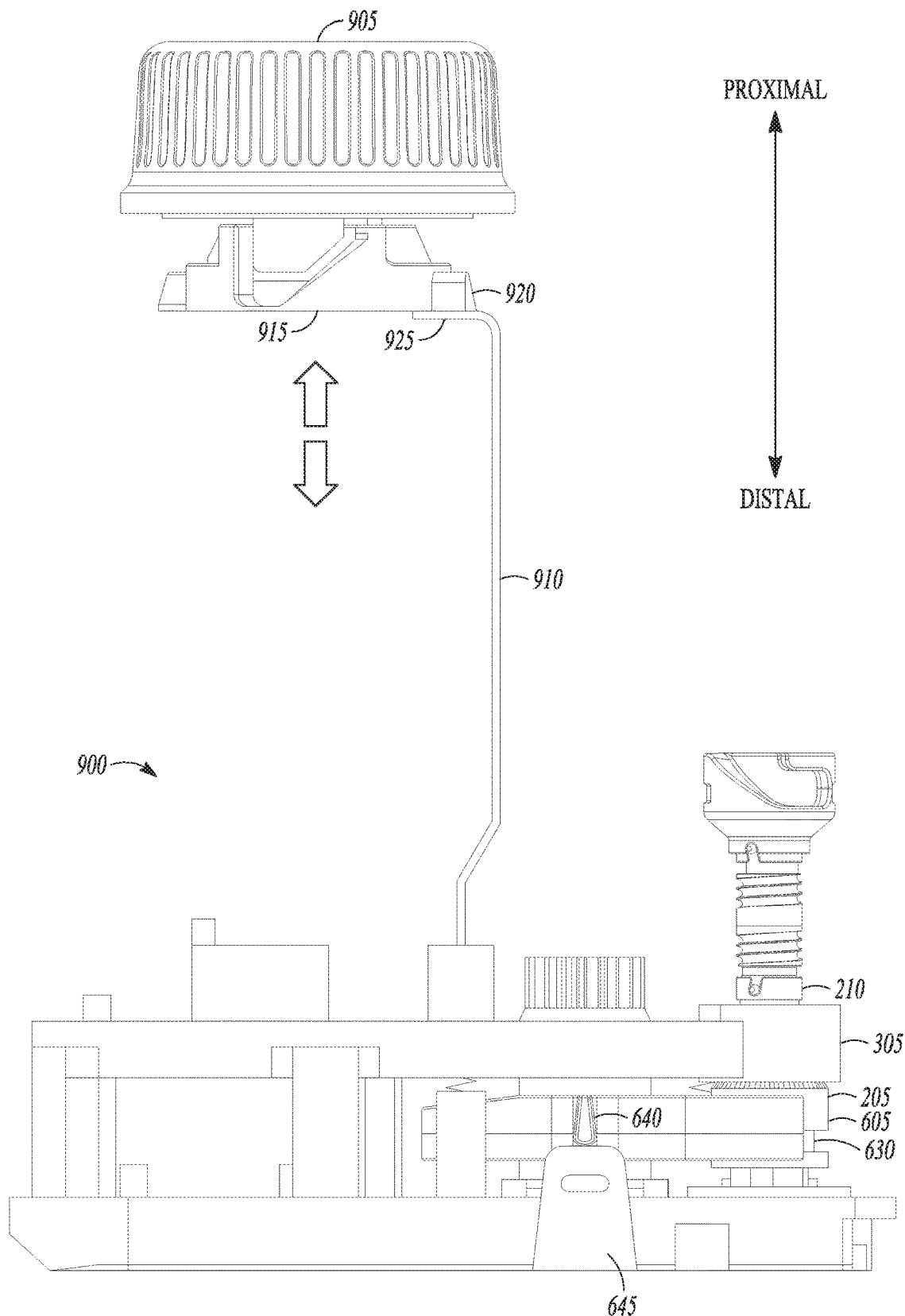
FIG. 9A is a schematic side view of a configuration with a lifter coupled to a control knob with an actuator.
Figure 9B:
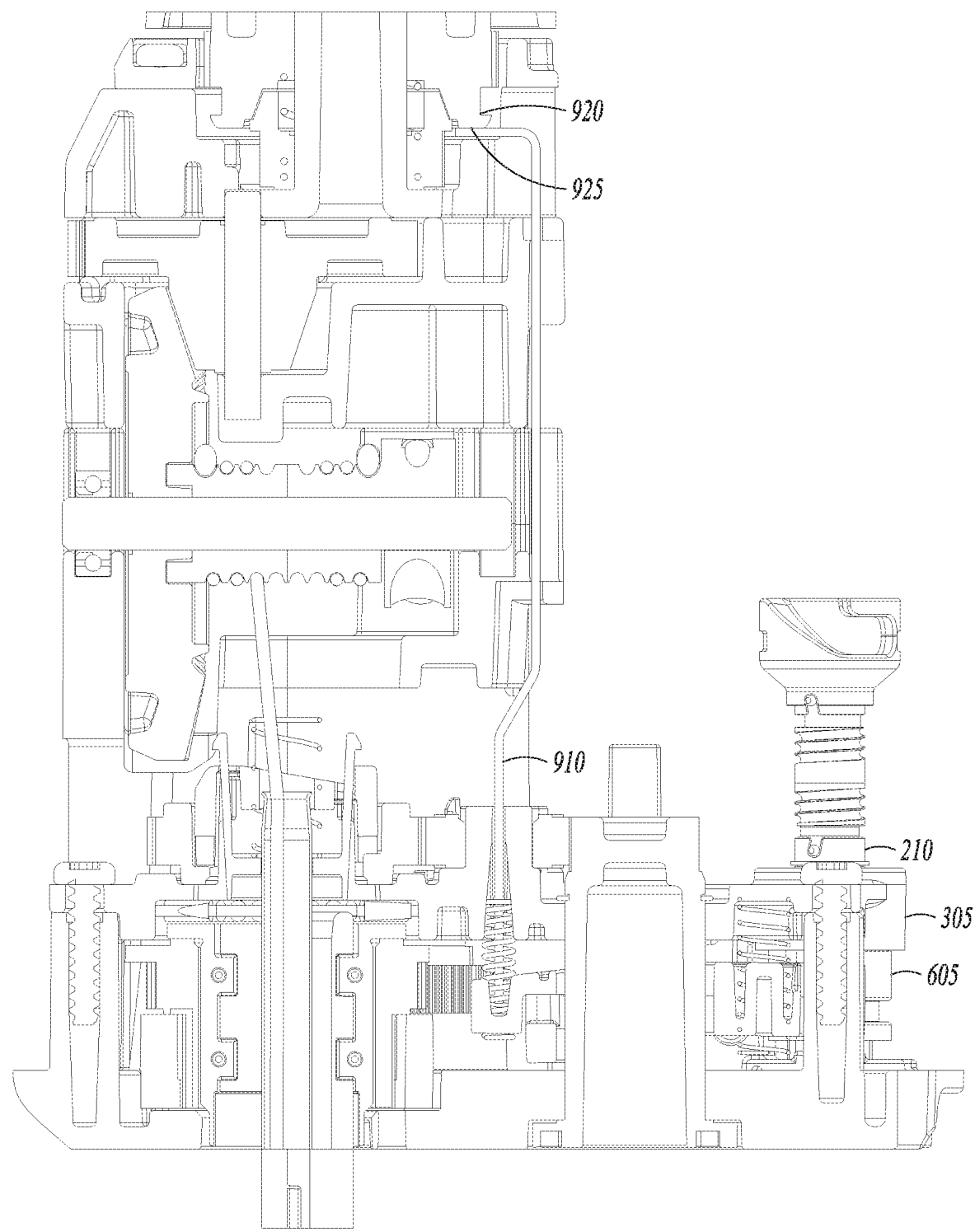
FIG. 9B is a cross-sectional view of a configuration with a lifter coupled to a control knob with an actuator.
Figure 9C:
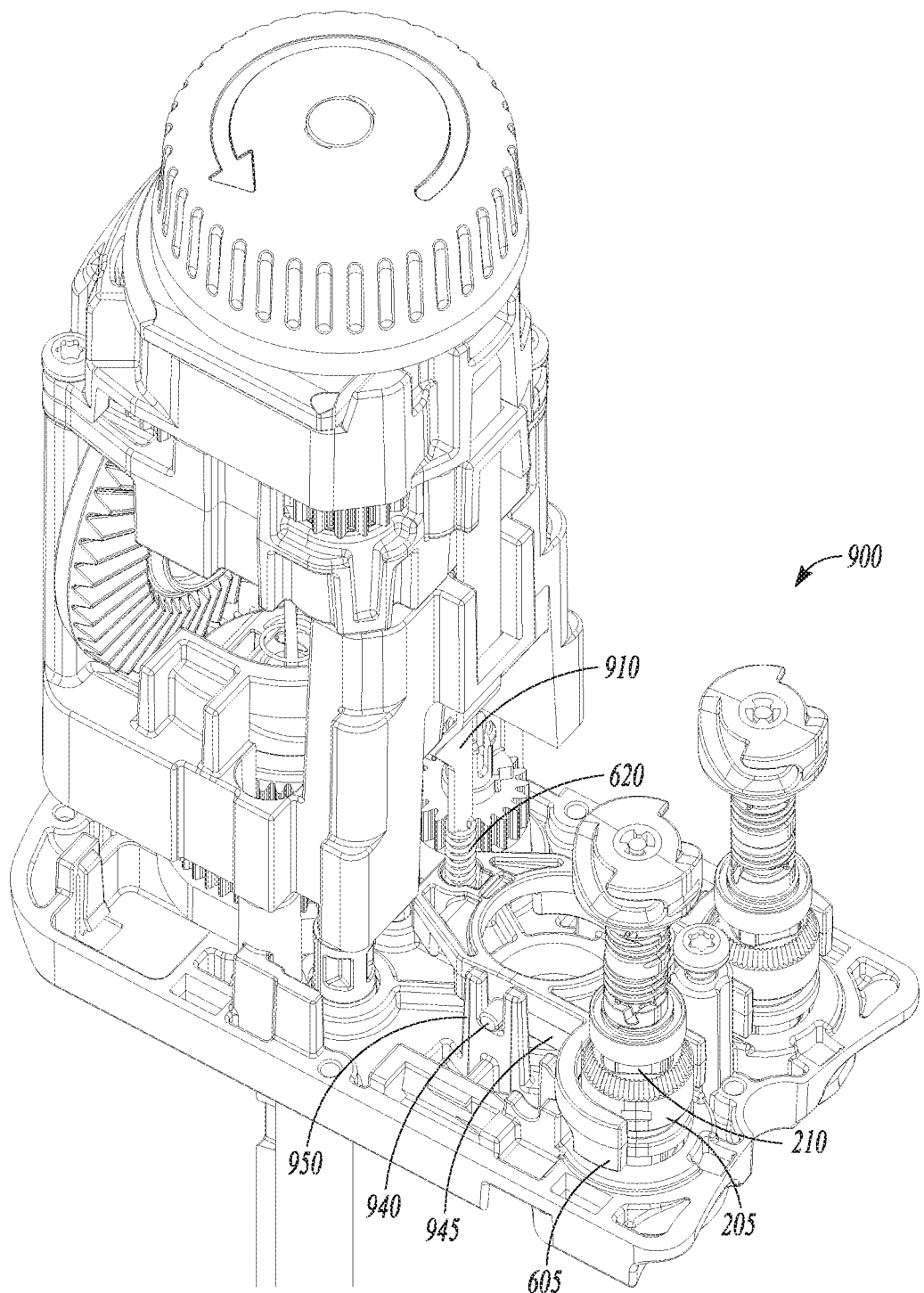
FIG. 9C is perspective view of the configuration shown in FIG. 9B.

FIG. 9A is a schematic side view of an example system 900 with the lifter 605 of FIG. 6 coupled to a manual input (e.g., control knob) 905 with an actuator 910. FIG. 9B is a cross-sectional view of the example system shown in FIG. 9A. FIG. 9C is perspective view of the configuration shown in FIG. 9A and FIG. 9B. As previously described, the first end 630 of the lifter 605 can be coupled to the locking device 605 such that upward movement of the first end presses the locking device 205 into engagement with the locking structure 305, and downward movement of the first end moves the locking device 205 downward out of engagement with the locking structure 305 to unlock the shaft 210. The lifter 605 may be coupled to the locking structure 305 with a pin 940, which may be fixed, or may slide in a slot 950, as shown in FIG. 9C. Actuator 910 may be coupled to the second end 635 of the lifter 605. The actuator 910 can and second end 630 may be biased upward by the spring, and pressed downward by coupling member 915. The coupling member may be biased against (e.g. by springs) or coupled to the manual input 905 and configured to move upward when the manual input 905 is turned a first direction (e.g. clockwise) and downward when the manual input 905 is turned in a second direction (e.g., counter-clockwise). The manual input 905 may be rotatably coupled to a structure that is also coupled to the locking structure, as shown in FIG. 9B.

In an example, rotation of the manual input 905 may engage one or more engagement features (e.g. first and second ramps) on the underside of the manual input 905 against one or more corresponding engagement features (e.g. third and fourth ramps) on a top surface of the coupling member 915 to slide the coupling member away from the manual input. The actuator may have a top surface 920 that is coupled to or rests against a bottom surface 925 of the coupling member 915, so that downward movement of the coupling member 915 causes downward movement of the actuator 910, which pivots the second end 635 of the lifter 605 down and moves the first end 630 of the lifter 605 up (as the lifter 605 rotates around pin 940), which engages the locking device 205 with the locking structure 305.

FIG. 9C is a perspective view of components of the locking system 900. A pivoting member 940 such as a pin may be coupled to a front side 945 the lifter 605 and positioned in a slot 950 that allows the lifter to pivot and move vertically, but restricts lateral movement. A second pin (not shown) may be coupled to a back side (not shown) of the lifter and positioned in a second slot (not shown) to provide a balanced pivoting axis. In configurations where the lifter is biased by a pushing member 645 (e.g. latch on an adaptor), the lifter may slide upward in the slot when the pushing member 645 engages the lifter 605.

In various configurations, the system 900 may be locked, or not locked, in a neutral state. When the system is not locked in a neutral state, operation of the manual input 905 may unlock the system (i.e. pivot the first end 630 up the lifter 605 up). When the system is locked in a neutral state, operation of the manual input may unlock the system (i.e. pivot the first end 630 of the lifter 605 down.)

In some examples, an adaptor for coupling to a computerized control system may include a pushing member 645 that biases the lifter from a neutral unlocked state to a neutral locked state by sliding the lifter and pin upward with respect to the slot.

Figure 10:
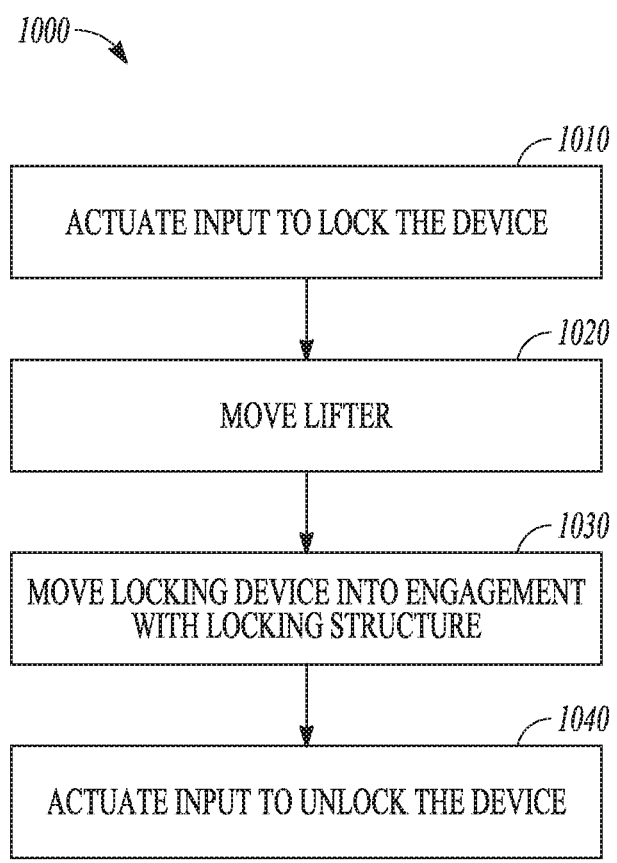
FIG. 10 is a flowchart illustration of an example method.

FIG. 10 is a flowchart illustration of an example method 1000 of locking an aspect of a medical device drive system. At step 1010, an input is actuated. For example, a knob may be rotated, a lever may be actuated, or a portion of an adapter may be inserted into a position on a chassis. At step 1020, a lifter is moved by the input. For example, the lifter may be pivoted, translated, or both. At step 1030, a locking device is moved by the lifter into engagement with a locking structure. In an example, the locking device is coupled to an end of the lifter, and the lifter presses the locking device into engagement with a locking structure. In an example, the locking device is coupled to a shaft, and moving the locking device into engagement with the locking structure prevents rotation of the shaft. At step 1040, the input is actuated in a first manner to unlock the device. For example, a knob rotated or lever may be actuated in an opposite direction from an actuation direction in step 1010.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second." and "third," etc. are used merely as labels, and are not intended to impose numerical requirements on their objects.

Geometric terms, such as "parallel", "perpendicular". "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A medical device drive system comprising:
   a locking structure;
   a locking device sized and shaped to engage with the locking structure, the locking device coupled to a drive system component;
   a lifter configured to actuate the locking device into and out of engagement with the locking structure;
   a rotary input; and
   a control knob coupled to the lifter,
   wherein the drive system component is selectively lockable by movement of the lifter,
   wherein the rotary input has an input feature that engages a portion of the lifter to pivot or translate the lifter and actuate the locking device, and
   wherein turning the knob moves the lifter to actuate the locking device.

2. The medical device drive system of claim 1, wherein the lifter is pivotably coupled to the locking structure, in a first state the lifter and locking device are pivoted toward the locking structure and the locking device is engaged with the locking structure to prevent rotational movement of the locking device relative to the locking structure, and in a second state the lifter and locking device are pivoted away from the locking structure and the locking device is not engaged with the locking structure.

3. The medical device drive system of claim 1, wherein the lifter is slidably coupled to the locking structure, wherein translating the lifter with respect to the locking structure actuates the locking device into and out of engagement with the locking structure.

4. The medical device drive system of claim 1, wherein the rotary input is configured to couple with a computerized control system.

5. The medical device drive system of claim 1, further comprising a manual release, wherein the control knob is configured to control both the locking device and the manual release.

6. The medical device drive system of claim 1, wherein the medical device drive system is configured to interface with an adaptor to operatively couple the drive system to a computerized control system.

7. The medical device drive system of claim 6, wherein in a first state the medical device drive system is not coupled to the adaptor and the lifter and locking device are in an unlocked position, the litter and locking device being actuatable to a locked position, and in a second state the medical device drive system is coupled to the adaptor, the adapter is engaged with the lifter, and the lifter and locking device are in a locked position, the lifter and locking device being actuatable to an unlocked position.

8. The medical device drive system of claim 7, wherein the lifter is pivotably coupled to the locking structure and in the second state the locking device is actuatable from the locked position to an unlocked position by manipulating an input that pivots the lifter.

9. The medical device drive system of claim 6, further comprising one or more springs engaged between the locking structure and the lifter, the one or more springs being compressed when the drive system is interfaced with the adaptor.

10. The medical device drive system of claim 1, wherein the locking device include a tapered structure that includes teeth that are sized and shaped to engage with corresponding teeth on a tapered recession in the locking structure.

11. The medical device drive system of claim 10, wherein the teeth on the tapered structure and the corresponding teeth on the tapered recession are sized and shaped to prevent rotation of the tapered structure with respect to the tapered recession but to allow the tapered structure to both translate and pivot away from the tapered recession.

12. A medical device drive system comprising:
   a locking structure;
   a locking device sized coupled to a drive system component and shaped to engage with the locking structure; and
   a lifter having an engagement end coupled to the locking device, the lifter being movable relative to the locking structure;
   wherein in a first state the engagement end of the lifter is biased toward the locking structure and the locking device is engaged with the locking structure such that the drive system component is not drivable, and in a second state the engagement end of the lifter is biased away from the locking structure and the locking device is disengaged from the locking structure such that the drive system component is drivable, and
   wherein the drive system component includes a steering control, the steering control being lockable by the locking device, the medical device drive system further comprising a manual release input, the manual release input being coupled to the lifter, wherein actuating the manual release locks the steering control.

13. The medical device drive system of claim 12, wherein the lifter is pivotable with respect to the locking structure to move the lifter and locking device between the first state and the second state.

* * * * *